United States Patent
Shreve et al.

(10) Patent No.: US 10,184,578 B2
(45) Date of Patent: Jan. 22, 2019

(54) STATIC BACK PRESSURE REGULATOR

(71) Applicant: Waters Technologies Corporation, Milford, MA (US)

(72) Inventors: Joshua A. Shreve, Franklin, MA (US); Charles T. Murphy, Norton, MA (US); Paul Keenan, Harrisville, RI (US); Ryan M. Hill, Watertown, MA (US); Sylvain Cormier, Mendon, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 401 days.

(21) Appl. No.: 14/382,400

(22) PCT Filed: Mar. 5, 2013

(86) PCT No.: PCT/US2013/029035
§ 371 (c)(1),
(2) Date: Sep. 2, 2014

(87) PCT Pub. No.: WO2013/134215
PCT Pub. Date: Sep. 12, 2013

(65) Prior Publication Data
US 2015/0129057 A1    May 14, 2015

Related U.S. Application Data

(60) Provisional application No. 61/608,320, filed on Mar. 8, 2012.

(51) Int. Cl.
*F16K 15/06* (2006.01)
*G05D 16/10* (2006.01)
(Continued)

(52) U.S. Cl.
CPC .............. *F16K 15/063* (2013.01); *F16K 1/38* (2013.01); *F16K 1/42* (2013.01); *F16K 15/021* (2013.01);
(Continued)

(58) Field of Classification Search
CPC .... F16K 15/063; F16K 15/021; F16K 15/044; F16K 1/38; F16K 1/42; F16K 25/005;
(Continued)

(56) References Cited

U.S. PATENT DOCUMENTS 511,650 A * 12/1893 Prusmann ........... F16K 17/0433
                                                        137/477
620,936 A *  3/1899 Kunzer ................. F16K 15/063
                                                        137/541
(Continued)

FOREIGN PATENT DOCUMENTS

CA    2563226 A1 *  5/2007  ........... F16K 15/063
DE    3415863 A1   10/1985
(Continued)

OTHER PUBLICATIONS

International Search Report for Application No. PCT/US2013/029035, dated May 8, 2013, 4 pages.
(Continued)

*Primary Examiner* — Craig Schneider
*Assistant Examiner* — Frederick D Soski
(74) *Attorney, Agent, or Firm* — Schmeiser, Olsen & Watts LLP

(57) ABSTRACT

The invention generally provides a static back pressure regulator. In exemplary embodiments, the static back pressure regulator includes a seat that defines part of a fluid pathway, a poppet, a spring arranged to bias the poppet toward the seat to restrict fluid flow through the fluid pathway, and a calibration element configured to adjust a
(Continued)

force applied to the poppet by the spring. The calibration element can include a through hole that forms part of the fluid pathway. The poppet can include a first guiding portion that extends into the through hole of the calibration element and inhibits tipping of the poppet relative to the seat.

25 Claims, 13 Drawing Sheets

(51) Int. Cl.
| | | |
|---|---|---|
| F16K 1/38 | (2006.01) | |
| F16K 1/42 | (2006.01) | |
| F16K 15/02 | (2006.01) | |
| F16K 15/04 | (2006.01) | |
| F16K 25/00 | (2006.01) | |
| F16K 25/04 | (2006.01) | |
| G01N 30/32 | (2006.01) | |
| B01D 15/40 | (2006.01) | |

(52) U.S. Cl.
CPC .......... *F16K 15/044* (2013.01); *F16K 25/005* (2013.01); *F16K 25/04* (2013.01); *G01N 30/32* (2013.01); *G05D 16/103* (2013.01); *B01D 15/40* (2013.01); *Y10T 137/7925* (2015.04)

(58) Field of Classification Search
CPC ...... F16K 25/04; G05D 16/103; B01D 15/40; Y10T 137/7925; Y10T 137/7847; Y10T 137/7744; Y10T 137/7746; Y10T 137/7747; Y10T 137/7878; Y10T 137/7904; Y10T 137/7922; Y10T 137/7929; G01N 30/32
USPC ................................ 251/318, 320–323, 333
See application file for complete search history.

(56) References Cited

U.S. PATENT DOCUMENTS

| | | | | |
|---|---|---|---|---|
| 1,380,094 A * | 5/1921 | Clark | F16K 17/04 | 137/473 |
| 2,109,202 A * | 2/1938 | Raney | F25B 41/062 | 137/100 |
| 2,597,057 A * | 5/1952 | Bergquist | F16K 17/0433 | 137/470 |
| 2,681,074 A * | 6/1954 | Frentzel | F16K 17/18 | 137/493 |
| 3,027,912 A * | 4/1962 | Carr | F22B 37/446 | 137/478 |
| 3,074,425 A * | 1/1963 | Kikendall | F16K 17/082 | 137/477 |
| 3,664,129 A * | 5/1972 | Schwab | F01P 7/044 | 137/468 |
| 3,687,153 A * | 8/1972 | Gold | F16L 19/048 | 137/112 |
| 3,756,273 A * | 9/1973 | Hengesbach | F16K 15/026 | 137/540 |
| 3,788,348 A * | 1/1974 | Johnson | F16L 37/23 | 137/542 |
| 3,788,352 A | 1/1974 | Anne et al. | | |
| 3,815,628 A * | 6/1974 | Ferrill | F16K 17/10 | 137/478 |
| 3,910,553 A * | 10/1975 | Boylan | F16K 1/54 | 251/205 |
| 3,945,396 A * | 3/1976 | Hengesbach | F16K 15/026 | 137/496 |
| 3,974,853 A * | 8/1976 | Bentley | A01G 25/023 | 137/503 |
| 4,007,593 A * | 2/1977 | Baker | B60T 13/162 | 60/405 |
| 4,108,204 A * | 8/1978 | Day | F16K 17/0466 | 137/543.13 |
| 4,114,851 A * | 9/1978 | Shivak | F16K 1/38 | 251/122 |
| 4,141,597 A * | 2/1979 | Sato | B60T 8/3225 | 303/115.1 |
| 4,251,226 A * | 2/1981 | Nishikawa | A62C 4/00 | 137/512.2 |
| 4,328,827 A * | 5/1982 | Enjolras | F16K 17/044 | 137/512.2 |
| 4,364,411 A * | 12/1982 | Payton | F16K 15/026 | 137/513.5 |
| 4,417,502 A * | 11/1983 | Shore | F15B 11/003 | 91/445 |
| 4,545,405 A * | 10/1985 | LaBelle | F16K 17/06 | 137/524 |
| 4,677,774 A * | 7/1987 | Macchi | D06F 75/06 | 251/214 |
| 4,721,129 A * | 1/1988 | Sousa | F16K 17/04 | 137/377 |
| 4,808,092 A * | 2/1989 | Funke | F04B 13/00 | 417/454 |
| 4,821,997 A | 4/1989 | Zdeblick | | |
| 4,977,927 A * | 12/1990 | Hill | F16K 15/044 | 137/539 |
| 5,052,433 A * | 10/1991 | Levenez | F15B 11/068 | 137/509 |
| 5,246,030 A * | 9/1993 | Jerina | F16K 17/0426 | 137/478 |
| 5,524,821 A | 6/1996 | Yie et al. | | |
| 5,556,075 A * | 9/1996 | Weber | F16K 1/34 | 251/282 |
| 5,623,962 A * | 4/1997 | Danzy | F16K 17/04 | 137/469 |
| 5,758,682 A * | 6/1998 | Cain | F16K 17/40 | 137/543.13 |
| 6,132,176 A * | 10/2000 | Higgins | B01D 25/005 | 137/538 |
| 6,148,536 A | 11/2000 | Iijima | | |
| 6,374,808 B1 * | 4/2002 | Fulford | F02M 57/025 | 123/458 |
| 6,516,765 B1 * | 2/2003 | Becker, Jr. | F01L 1/32 | 123/188.9 |
| 8,701,707 B2 | 4/2014 | Moosmann et al. | | |
| 2002/0170601 A1 * | 11/2002 | Smith | G05D 16/10 | 137/505.42 |
| 2003/0047216 A1 * | 3/2003 | Kelly | F16K 17/06 | 137/538 |
| 2004/0045607 A1 * | 3/2004 | Lammers | F16K 15/063 | 137/543 |
| 2006/0065198 A1 * | 3/2006 | Meads | A01J 3/00 | 119/14.47 |
| 2006/0237064 A1 * | 10/2006 | Benson | F16K 1/36 | 137/487.5 |
| 2006/0278280 A1 * | 12/2006 | Yang | F16K 15/063 | 137/542 |
| 2007/0044848 A1 * | 3/2007 | Norman | F16K 15/063 | 137/542 |
| 2009/0044871 A1 * | 2/2009 | Courtright | F16K 15/044 | 137/485 |
| 2009/0314009 A1 * | 12/2009 | Campeau | F16K 1/305 | 62/48.1 |
| 2009/0314359 A1 * | 12/2009 | Woelfges | F16K 17/105 | 137/492.5 |
| 2010/0101672 A1 * | 4/2010 | Roys | F16K 11/07 | 137/884 |
| 2011/0147016 A1 * | 6/2011 | Blease | A62C 35/68 | 169/17 |
| 2012/0266980 A1 * | 10/2012 | Olbrisch | E21B 34/10 | 137/515 |

FOREIGN PATENT DOCUMENTS

| | | |
|---|---|---|
| DE | 9016836 U1 | 2/1991 |
| DE | 102007031296 A1 | 1/2009 |
| EP | 904844 A1 | 3/1999 |

(56) References Cited

FOREIGN PATENT DOCUMENTS

| EP | 2699975 A1 | 2/2014 | | |
|---|---|---|---|---|
| GB | 951761 A | * | 3/1964 | ............... F16K 1/38 |
| GB | 2045375 A | * | 10/1980 | .............. F16L 37/38 |
| WO | 03/102452 A1 | 12/2003 | | |
| WO | 03/102454 A1 | 12/2003 | | |
| WO | 2009/092488 A1 | 7/2009 | | |
| WO | 2011157985 | 12/2011 | | |

OTHER PUBLICATIONS

International Written Opinion Report for Application No. PCT/US2013/029035, dated May 8, 2013, 16 pages.
German Office Action dated Oct. 10, 2015 for Application No. 11 2013 001 329.0.
Office Action dated Dec. 9, 2016 by UK Intellectual Property Office for Application No. GB1415041.1 (9 pages).

\* cited by examiner

STATIC BACK PRESSURE REGULATOR

RELATED APPLICATIONS

This application is the National Stage of International Application No. PCT/US2013/029035, filed on Mar. 5, 2013, which claims priority to and benefit of U.S. Provisional Patent Application No. 61/608,320 entitled "Static Back Pressure Regulator," filed Mar. 8, 2012. The contents and teachings of each of these applications are hereby expressly incorporated herein by reference in their entirety.

TECHNICAL FIELD

This disclosure relates to back pressure regulation, and, in one particular implementation, to a static back pressure regulator for a supercritical fluid chromatography system.

BACKGROUND

Supercritical fluid chromatography (SFC) is a chromatographic separation technique that typically utilizes liquefied carbon dioxide ($CO_2$) as a mobile phase solvent. In order to keep the mobile phase in liquid (or liquid-like density) form, the chromatographic flow path is pressurized; typically to a pressure of at least 1100 psi.

SUMMARY

A static back pressure regulator is utilized to provide a substantially constant back pressure over the operating range of a supercritical fluid chromatography (SFC) system. The static back pressure regulator must survive the destructive environment of $CO_2$/co-solvent mixtures and the rapid decompression of $CO_2$ during its phase change through the restrictive aperture of the static back pressure regulator.

One aspect features a static back pressure regulator that includes a seat that defines part of a fluid pathway, a poppet, a spring arranged to bias the poppet toward the seat to restrict fluid flow through the fluid pathway, and a calibration element configured to adjust a force applied to the poppet by the spring. The calibration element includes a through hole that forms part of the fluid pathway. The poppet comprises a first guiding portion that extends into the through hole of the calibration element and inhibits tipping of the poppet relative to the seat.

Another aspect provides a static back pressure regulator that includes a seat that defines a part of a fluid pathway, a poppet, and a spring arranged to bias the poppet toward the seat to restrict fluid flow through the fluid pathway. The poppet includes a guiding portion that extends into the spring and thereby inhibits buckling of the spring.

According to another aspect, a static back pressure regulator includes a housing defining a cavity which forms part of a fluid pathway, a seat supported by the housing and defining part of the fluid pathway, a poppet disposed within the cavity and displaceable relative to the seat to restrict fluid flow through the fluid pathway, and a damping member disposed between the housing and the poppet and arranged to absorb energy and inhibit vibration of the poppet.

Yet another aspect provides a static back pressure regulator that includes a housing defining a cavity which forms part of a fluid pathway, a seat supported by the housing and defining part of the fluid pathway, and a poppet disposed within the cavity and displaceable relative to the seat to restrict fluid flow through the fluid pathway. The poppet has a flow channel arranged on a side of the poppet so as to cause a biasing of the poppet, as fluid flows through the fluid pathway, such that vibration of the poppet is inhibited.

A further aspect features a static back pressure regulator that includes a housing defining a cavity which forms part of a fluid pathway, a seat supported by the housing and defining part of the fluid pathway, and a poppet disposed within the cavity and displaceable relative to the seat to restrict fluid flow through the fluid pathway. The housing has helical grooves along the cavity to cause a vortex around the poppet, as fluid flows through the fluid pathway, such that vibration of the poppet is inhibited.

In accordance with another aspect a static back pressure regulator includes a housing defining a cavity which forms part of a fluid pathway, a seat supported by the housing and defining part of the fluid pathway, and a poppet disposed within the cavity and displaceable relative to the seat to restrict fluid flow through the fluid pathway. The poppet is at least partially formed of a chemically resistant ceramic.

Yet another aspect features a static back pressure regulator that includes: a housing defining a cavity which forms part of a fluid pathway, a seat supported by the housing and defining part of the fluid pathway, and a poppet disposed within the cavity and displaceable relative to the seat to restrict fluid flow through the fluid pathway. The poppet includes a metal plating.

Implementations can include one or more of the following features.

In some implementations, the poppet includes a guiding portion (e.g., a second guiding portion) that extends into the spring and thereby inhibits buckling of the spring.

In certain implementations, the static back pressure regulator includes a damping member arranged to absorb energy and inhibit vibration of the poppet.

In some implementations, the static back pressure regulator includes a housing defining a cavity forming part of the fluid pathway. The poppet is disposed within the cavity, and the damping member is disposed between the housing and the poppet.

In certain implementations, the damping member includes an o-ring gasket.

In some implementations, the damping member is formed of an elastomer.

In certain implementations, the damping member is disposed between the calibration element and the poppet (e.g., between the calibration element and the first guiding portion of the poppet).

In some implementations, the poppet has a flow channel arranged on a side of the poppet so as to cause a biasing of the poppet, as fluid flows through the fluid pathway, such that vibration of the poppet is inhibited.

In certain implementations, the static back pressure regulator includes a housing defining a cavity forming part of the fluid pathway. The poppet is disposed within the cavity, and the housing has helical grooves along the cavity to cause a vortex around the poppet, as fluid flows through the fluid pathway, such that vibration of the poppet is inhibited.

In some implementations, the poppet includes a tip, and a stem.

In certain implementations, the stem includes the first guiding portion.

In some implementations, the stem defines a recess for receiving the tip.

In certain implementations, the stem is integral with the tip.

In some implementations, the tip is at least partially formed of a chemically resistant ceramic (e.g., zirconia, ruby, or sapphire).

In some implementations, the tip is spherical.

In certain implementations the poppet comprises a metal plating (e.g., a gold plating and a platinum plating).

In some implementations, the poppet has a conical portion that contacts the seat.

In certain implementations, the conical portion has an included angle of about 20 degrees to about 90 degrees (e.g., about 20 degrees to about 60 degrees).

In some implementations, the poppet includes a substantially flat surface for contacting the seat to inhibit fluid flow, and a boss that extends outwardly from the substantially flat surface for engaging a through hole in the seat, thereby to center the poppet relative to the seat.

In certain implementations, the seat is at least partially formed of a polymer (e.g., polyimide or polyether-ether-ketone).

Implementations may provide one or more of the following advantages.

Some implementations provide a static back pressure regulator that can survive an environment in which $CO_2$ phase changes with a co-solvent mixture that can cause both corrosion and erosion.

Other aspects, features, and advantages are in the description, drawings, and claims.

BRIEF DESCRIPTION OF THE DRAWINGS

Like reference numbers indicate like elements.

DETAILED DESCRIPTION

System Overview

Figure 1:
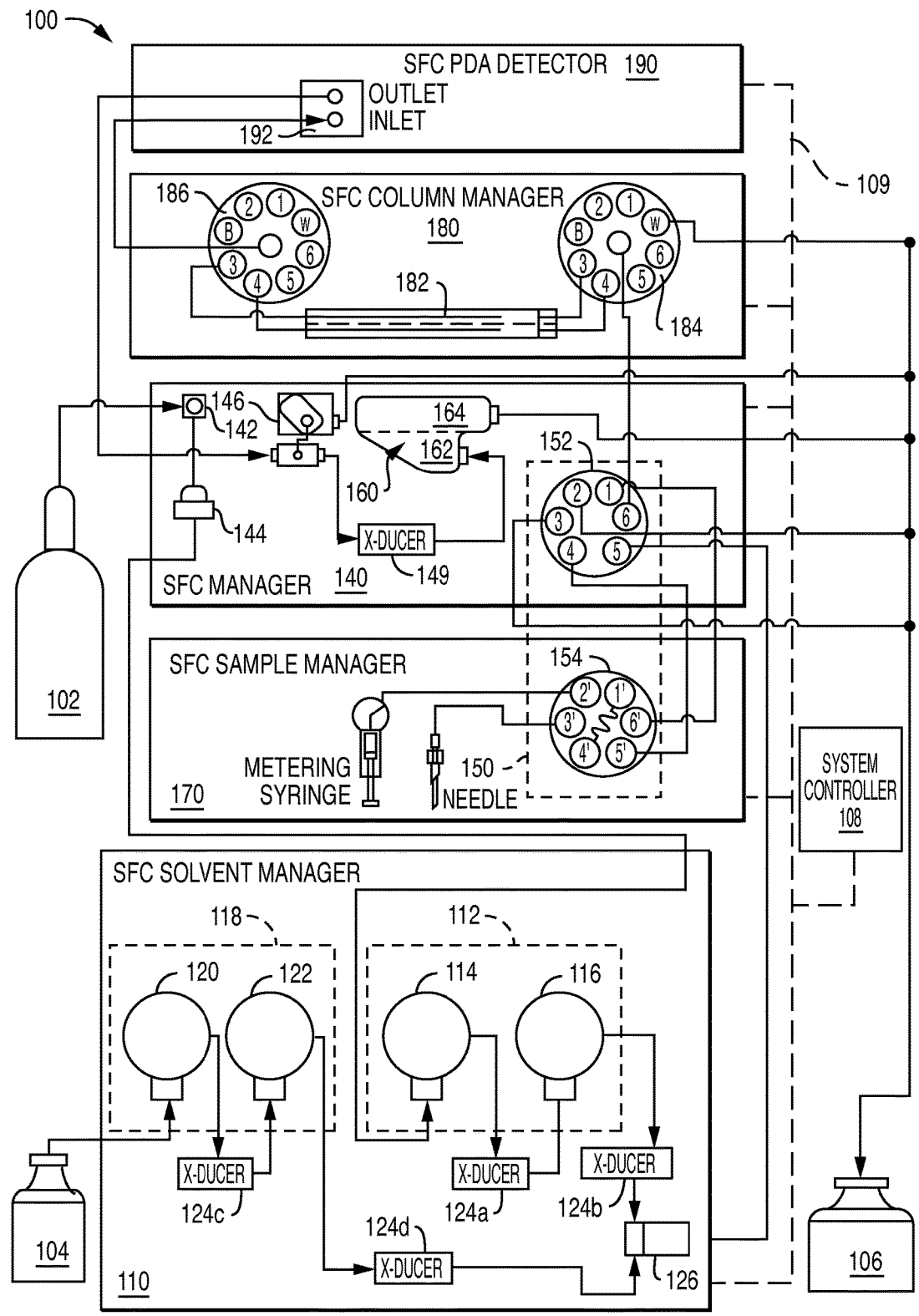
FIG. 1 is a schematic view of a supercritical fluid chromatography (SFC) system.

FIG. 1 schematically depicts a supercritical fluid chromatography (SFC) system 100. The SFC system 100 includes a plurality of stackable modules including a solvent manager 110; an SFC manager 140; a sample manager 170; a column manager 180; and a detector module 190.

The solvent manager 110 is comprised of a first pump 112 which receives carbon dioxide ($CO_2$) from $CO_2$ source 102 (e.g., a tank containing compressed $CO_2$). The $CO_2$ passes through an inlet shutoff valve 142 and a filter 144 in the SFC manager 140 on its way to the first pump 112. The first pump 112 can comprise one or more actuators each comprising or connected to cooling means, such as a cooling coil and/or a thermoelectric cooler, for cooling the flow of $CO_2$ as it passes through the first pump 112 to help ensure that the $CO_2$ fluid flow is deliverable in liquid form. In some cases, the first pump 112 comprises a primary actuator 114 and an accumulator actuator 116. The primary and accumulator actuators 114, 116 each include an associated pump head, and are connected in series. The accumulator actuator 116 delivers $CO_2$ to the system 100. The primary actuator 114 delivers $CO_2$ to the system 100 while refilling the accumulator actuator 116.

In some cases, the solvent manager 110 also includes a second pump 118 for receiving an organic co-solvent (e.g., methanol, water ($H_2O$), etc.) from a co-solvent source 104 and delivering it to the system 110. The second pump 118 can comprise a primary actuator 120 and an accumulator actuator 122, each including an associated pump head. The primary and accumulator actuators 120, 122 of the second pump 118 are connected in series. The accumulator actuator 122 delivers co-solvent to the system 100. The primary actuator 120 delivers co-solvent to the system 100 while refilling the accumulator actuator 122.

Transducers 124a-d are connected to outlets of the respective pump heads for monitoring pressure. The solvent manager 110 also includes electrical drives for driving the primary actuators 114, 120 and the accumulator actuators 116, 122. The $CO_2$ and co-solvent fluid flows from the first and second pumps 112, 118, respectively, and are mixed at a tee 126 forming a mobile phase fluid flow that continues to an injection valve subsystem 150, which injects a sample slug for separation into the mobile phase fluid flow.

In the illustrated example, the injection valve subsystem 150 is comprised of an auxiliary valve 152 that is disposed in the SFC manager 140 and an inject valve 154 that is disposed in the sample manager 170. The auxiliary valve 152 and the inject valve 152 are fluidically connected and the operations of these two valves are coordinated to introduce a sample plug into the mobile phase fluid flow. The inject valve 154 is operable to draw up a sample plug from a sample source (e.g., a vial) in the sample manager 170 and the auxiliary valve 152 is operable to control the flow of mobile phase fluid into and out of the inject valve 154. The SFC manager 140 also includes a valve actuator for actuating the auxiliary valve 152 and electrical drives for driving the valve actuations. Similarly, the sample manager 170 includes a valve actuator for actuating the inject valve and 154 and electrical drives for driving the valve actuations.

From the injection valve subsystem 150, the mobile phase flow containing the injected sample plug continues through a separation column 182 in the column manager 180, where the sample plug is separated into its individual component parts. The column manager 180 comprises a plurality of such separation columns, and inlet and outlet switching valves 184, 186 for switching between the various separation columns.

After passing through the separation column 182, the mobile phase fluid flow continues on to a detector 192 (e.g., a flow cell/photodiode array type detector) housed within the detector module 190 then through a vent valve 146 and then on to a back pressure regulator assembly 160 in the SFC manager 140 before being exhausted to waste 106. A transducer 149 is provided between the vent valve 146 and the back pressure regulator assembly 160.

The back pressure regulator assembly 160 includes a dynamic (active) back pressure regulator 162 and a static (passive) back pressure regulator 164 arranged in series. The dynamic back pressure regulator 162, which is discussed in greater detail below, is adjustable to control or modify the system fluid pressure. This allows the pressure to be changed from run to run. The properties of CO2 affect how quickly compounds are extracted from the column 182, so the ability to change the pressure can allow for different separation based on pressure.

The static back pressure regulator 164 is a passive component (e.g., a check valve) that is set to above the critical pressure, to help ensure that the CO2 is liquid through the dynamic back pressure regulator 162. The dynamic back pressure regulator 162 can control more consistently when it is liquid on both the inlet and the outlet. If the outlet is gas, small reductions in the restriction can cause the CO2 to gasify upstream of the dynamic back pressure regulator 162 causing it to be unable to control. In addition, this arrangement helps to ensure that the static back pressure regulator 164 is the location of phase change. The phase change is endothermic, therefore the phase change location may need to be heated to prevent freezing. By controlling the location of phase change, the heating can be simplified and localized to the static back pressure regulator 164.

Generally, the static back pressure regulator 164 is designed to keep the pressure at the outlet of the dynamic back pressure regulator 162 below 1500 psi but above the minimum pressure necessary to keep the CO2 in liquid phase. In some cases, the static back pressure regulator 164 is designed to regulate the pressure within the range of about 1150 psi (at minimum flow rate) to about 1400 psi (at maximum flow rate). The dynamic back pressure regulator 162 can be used to regulate system pressure in the range of about 1500 psi to about 6000 psi.

Also shown schematically in FIG. 1 is a computerized system controller 108 that can assist in coordinating operation of the SFC system 100. Each of the individual modules 110, 140, 170, 180, 190 also includes its own control electronics, which can interface with each other and with the system controller 108 via an Ethernet connection 109. The control electronics for each module can include non-volatile memory with computer-readable instructions (firmware) for controlling operation of the respective module's components (e.g., the pumps, valves, etc.) in response to signals received from the system controller 108 or from the other modules. Each module's control electronics can also include at least one processor for executing the computer-readable instructions, receiving input, and sending output. The control electronics can also include one or more digital-to-analog (D/A) converters for converting digital output from one of the processors to an analog signal for actuating an associated one of the pumps or valves (e.g., via an associated pump or valve actuator). The control electronics can also include one or more analog-to-digital (A/D) converters for converting an analog signal, such as from system sensors (e.g., pressure transducers), to a digital signal for input to one of the processors. In some cases, some or all of the various features of these control electronics can be integrated in a microcontroller.

Static Back Pressure Regulator

Figure 2:
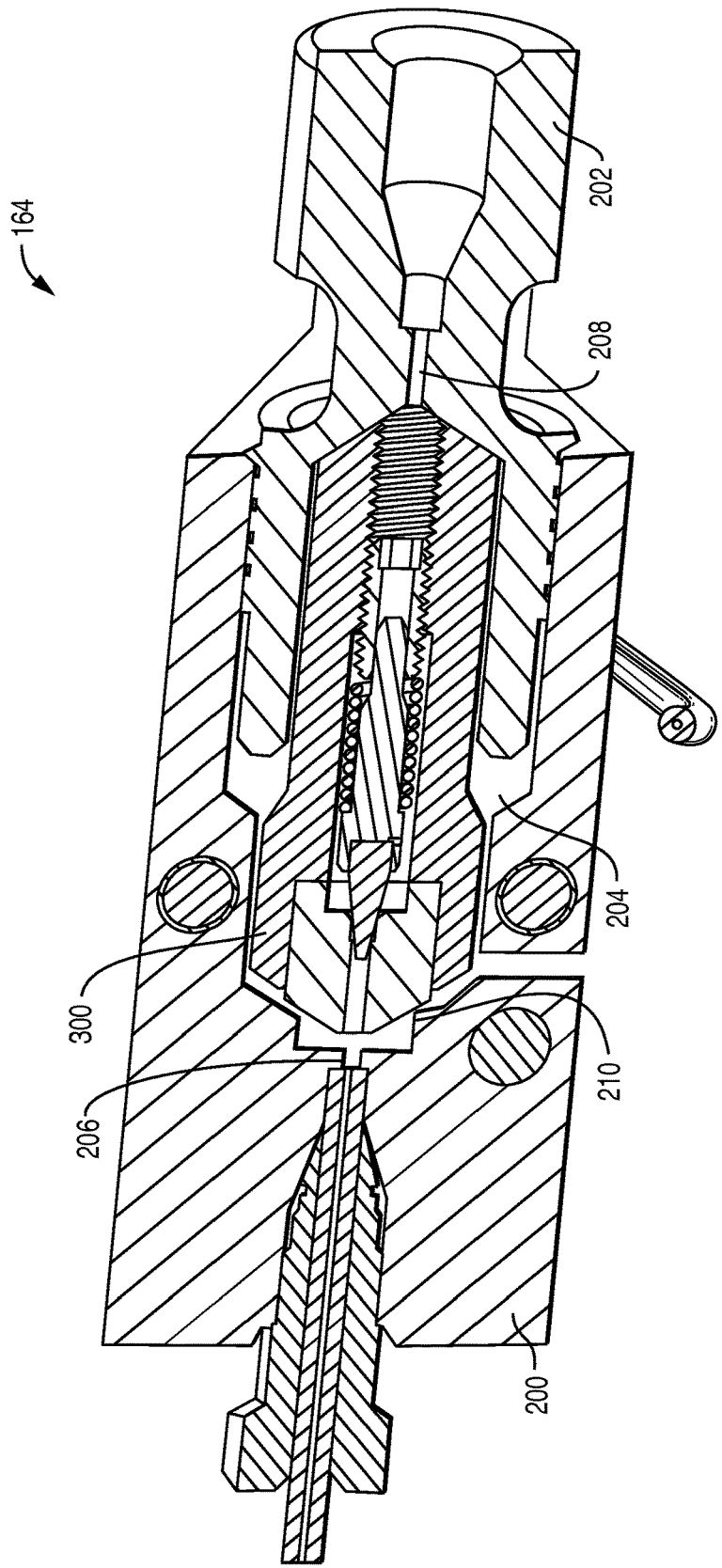
FIG. 2 is a cross-sectional view of a static back pressure regulator from the SFC system of FIG. 1.

Referring to FIG. 2, the static back pressure regulator 164 includes a main housing 200, a retaining nut 202; and a cartridge 300 that is disposed within a cavity 204 defined by the main housing 200 and the retaining nut 202. The retaining nut 202 is threadedly received in the main housing 200 to secure the cartridge therebetween.

In use, high pressure fluid enters the static back pressure regulator 164 through an inlet port 206 in the main housing 200, passes through the cartridge 300 (assuming the fluid pressure exceeds the set point pressure of the static back pressure regulator 164), and then is exhausted through an outlet port 208 in the retaining nut 202

Figure 3A:
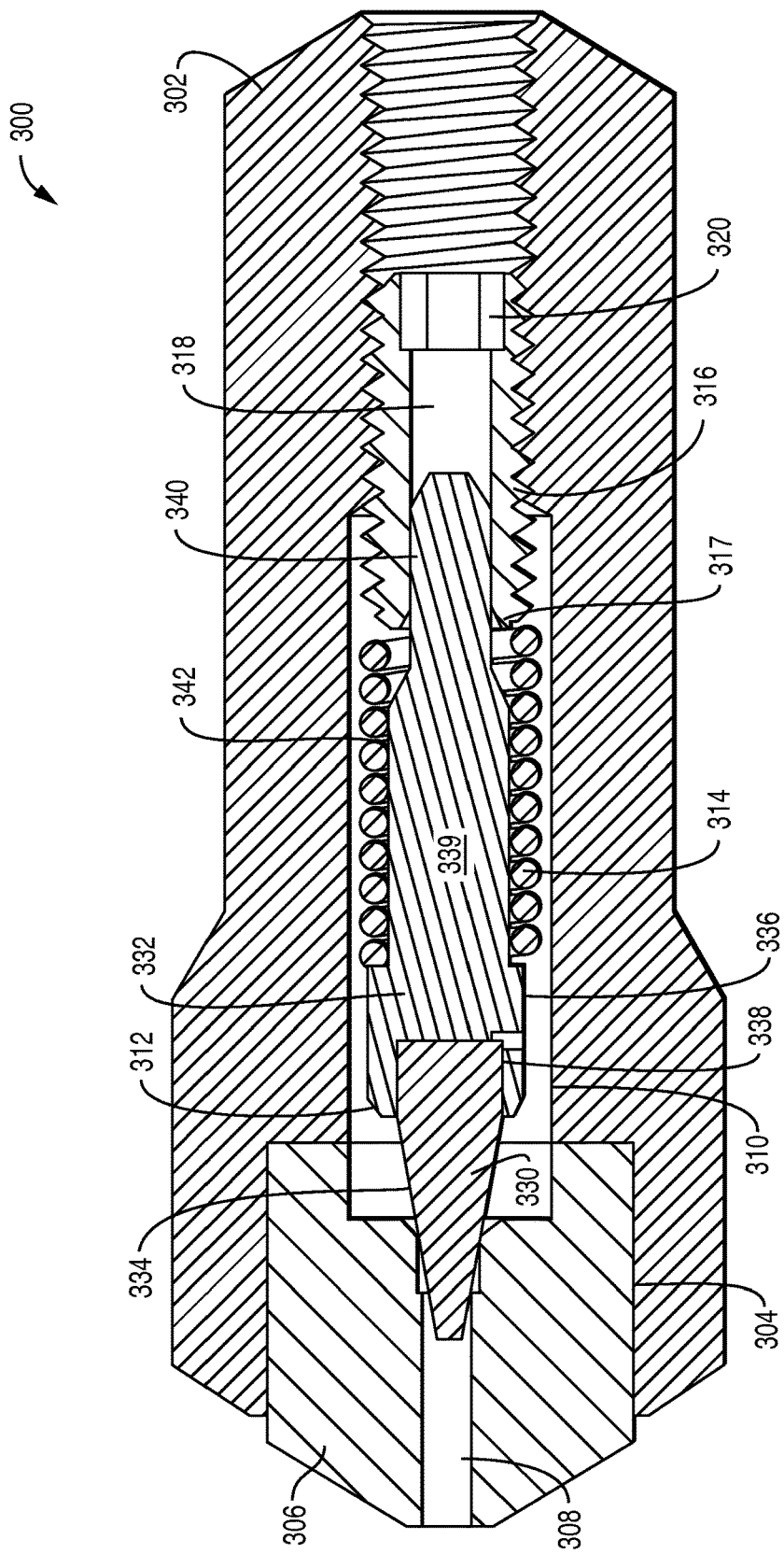
FIGS. 3A and 3B are cross-sectional views of embodiments of a cartridge of the static back pressure regulator of FIG. 2.
Figure 3B:
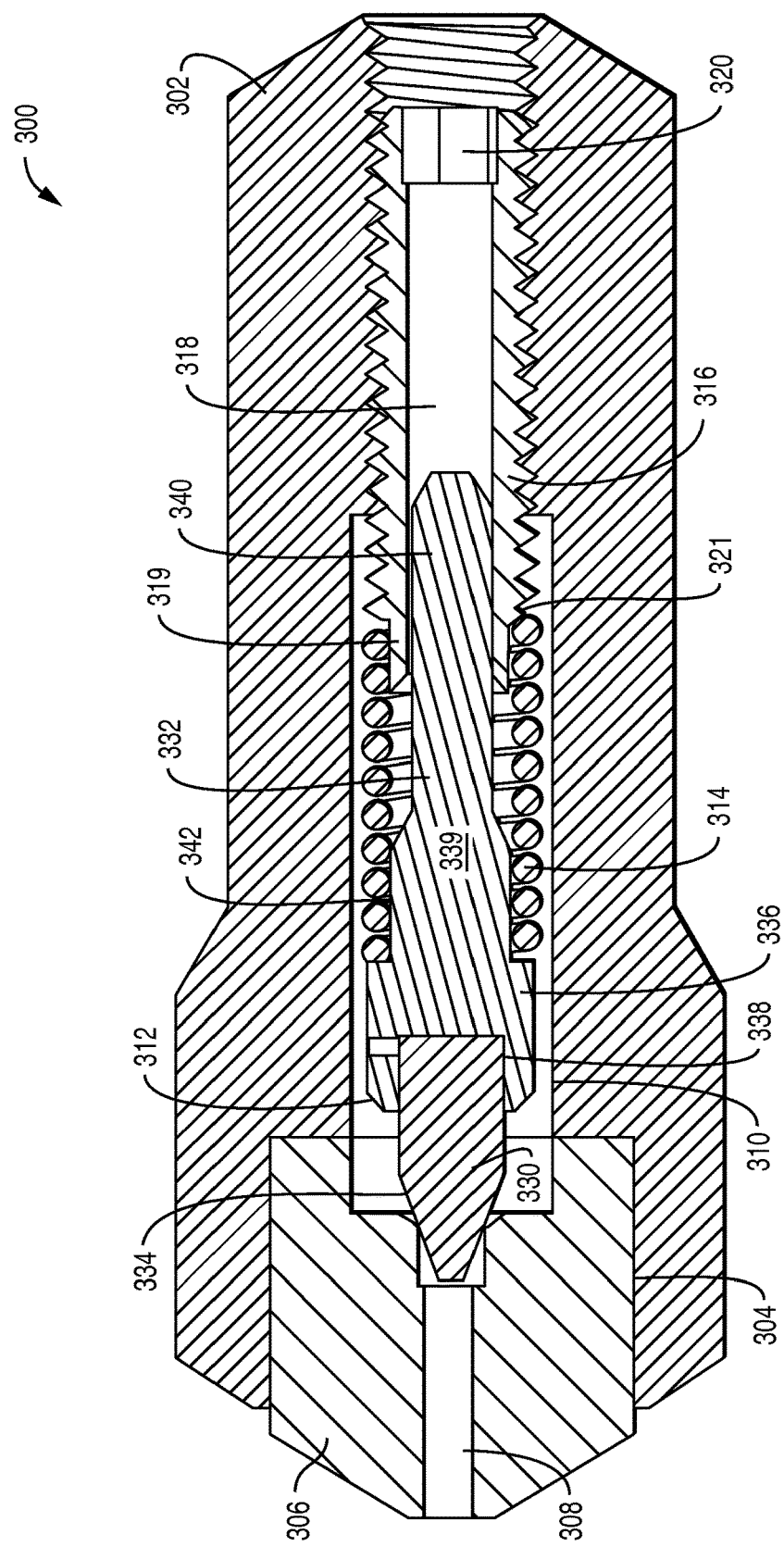

Referring to FIGS. 3A and 3B, the cartridge 300 includes a cartridge housing 302 that defines a recess 304 for receiving a seat 306 at an inlet end of the cartridge 300. The seat 306 includes a through hole 308 that is in fluidic communication with a cavity 310 defined in the cartridge housing 302. The seat 306 is held in place within the recess 304 via the engagement between the retaining nut 202 (FIG. 2) and the main housing 200 (FIG. 2). The main housing 200 (FIG. 2) includes a sharp corner 210 that bites into a tapered end of the seat 306. The seat 306 is at least partially formed of a polymer, such as polyimide (available as Dupont Vespel SCP-5000 polyimide) or polyether-ether-ketone, such as PEEK polymer (available from Victrex PLC, Lancashire, United Kingdom). In some cases, the polymer forming the seat 306 can be filled with carbon fiber.

The cartridge 300 also includes a poppet 312 that is disposed within and is displaceable along a longitudinal axis of the cartridge housing 302. A spring 314 (e.g., a helical compression spring) is disposed within the cavity 310 and is arranged to bias the poppet 312 toward the seat 306, thereby to restrict fluid flow through the cartridge 300. A calibration screw 316 is threadedly received within an outlet end of the cartridge housing 302. In exemplary embodiments, the calibration screw 316 and the spring 314 can be configured to avoid engagement between the threads of the screw and the helix of the spring. For example, direction of the spring helix can be opposite to the direction of the screw thread, i.e., the screw can have right handed threads and the spring can be left hand wound or the screw can have left handed threads and the spring can be right hand wound. The calibration screw 316 is adjustable, by tightening or loosening it relative to the cartridge housing 302, to set the compressive force acting on the spring 314 and thereby setting the restriction of the static back pressure regulator 164. One or both of the ends of the spring 314 can be closed and ground flat. The calibration screw 316 includes a through hole 318 that allows for the passage of fluid, and a hex or star shaped recess 320 is provided at a distal end of the through hole 318 which allows the position of the calibration screw 316, relative to the cartridge housing, to be adjusted with a tool.

As shown in the exemplary embodiment of FIG. 3A, the calibration screw 316 can include a conical surface 317. The conical surface 317 at the end of the screw 316 can engage the spring 314 and stabilize the interface between the screw 316 and the spring 314. For example, the conical surface 317 can maintain the alignment between the screw 316 and the spring 314. In some cases, the conical surface 317 can have a slight interference fit with the spring 314. This interference fit can help to prevent the spring 314 from creating a significant side loading of the poppet 312. As discussed in more detail below, the conical surface 317 can also limit buckling of the spring 314.

As shown in the exemplary embodiment of FIG. 3B, the calibration screw 316 can include a protrusion 319. The protrusion 319 extends from an end of the calibration screw 316 and engages the spring 314. In some embodiments, the protrusion 319 can extend into the spring 314. The protrusion 319 can stabilize the interface between the screw 316 and the spring 314. For example, the protrusion 319 can maintain the alignment between the screw 316 and the spring 314. The protrusion 319 can have an outer diameter that is close to or substantially the same as the inner diameter of the spring 314. In some cases, the protrusion 319 can have a slight interference fit with the spring 314. This interference fit can help to prevent the spring 314 from creating a significant side loading of the poppet 312. As discussed in more detail below, the protrusion 319 can also limit buckling of the spring 314. The calibration screw can also include a flat portion 321 disposed adjacent to the protrusion 319. The flat portion 321 can have a surface extending substantially perpendicular to the longitudinal axis of the screw 316. The flat portion 321 can limit side loading of the spring 314 by providing a flat contact surface for engagement with the end of the spring 314. For example, the flat portion 321 can contact the closed and ground end of the spring 314.

High pressure fluid enters into the cartridge through the through hole 308 in the seat 306. If the fluid pressure is high enough to overcome the spring force, the fluid will displace the poppet 312 away from the seat 306 and then pass into the cavity 310 in the cartridge housing 302 and exits through the through hole 318 in the calibration screw 316.

The poppet 312 includes a tip 330 and a stem 332. The tip 330 is formed of a ceramic material, such as zirconia, sapphire, or ruby. In some implementations, the tip 330 can include a tapered (cone) portion 334 that engages the seat 306 to stop flow and which forms a restriction region with the seat 306 when in an open condition. The tapered portion 334 can have an included angle of about 20 degrees to about 90 degrees (e.g., about 20 degrees to about 90 degrees). An included angle of about 20 degrees to about 60 degrees can assist in centering with the through hole 308 in the seat 306 but may not yield the seat 306. Blunter angles will slowly close up the hole as the seat yields or creeps.

The stem 332 includes a head 336 which defines a recess 338 for receiving the tip 330. The tip 330 has the same diameter as the recess 338 for a zero gap fit or slight press fit between the tip 330 and the recess 338. The tip 330 is held in place by the force of the spring 314 holding the poppet 312 against the seat 306 and/or by fluid pressure that displaces the poppet 312 away from the seat 306. The spring 314 contacts the head 336 to apply the force on the poppet 312.

The stem 332 also includes a shaft 339 which extends outwardly from the head 336. The shaft 339 includes a first guiding portion 340 that extends into the through hole 318 in the calibration screw 316 with sufficient clearance to permit fluid flow through the through hole 318. In some cases, the calibration screw 316 and/or the first guiding portion 340 may include surface grooves that facilitate fluid flow through the through hole 318. By extending the first guiding portion 340 of the shaft 339 into the through hole 318 in the calibration screw 316, the shaft 339 can be guided to prevent excessive tipping.

The shaft 339 also includes a second guiding portion 342 that has a diameter that is close to or substantially the same as the inner diameter of the spring 314. The spring 314 typically has a fairly high length to diameter ratio making it very susceptible to buckling. By making the second guiding portion 342 of the shaft 339 a diameter that is close to or substantially the same as the inner diameter of the spring 314, the buckling is limited. In some cases, the second guiding portion 342 can have a slight interference fit with the spring 314. This interference fit can help to prevent asymmetry of the end of the spring 314 from creating a significant side loading of the poppet 312. In embodiments having a protrusion 319 and/or a flat portion 321, e.g., as shown in FIG. 3B, the second guiding portion 342, the protrusion 319, and/or the flat portion 321 can work in conjunction to limit buckling of the spring 314 and prevent side loading of the poppet 312. In such cases, the length of the second guiding portion can be reduced, thereby providing a greater adjustment range of the calibration screw 316.

Figure 4A:
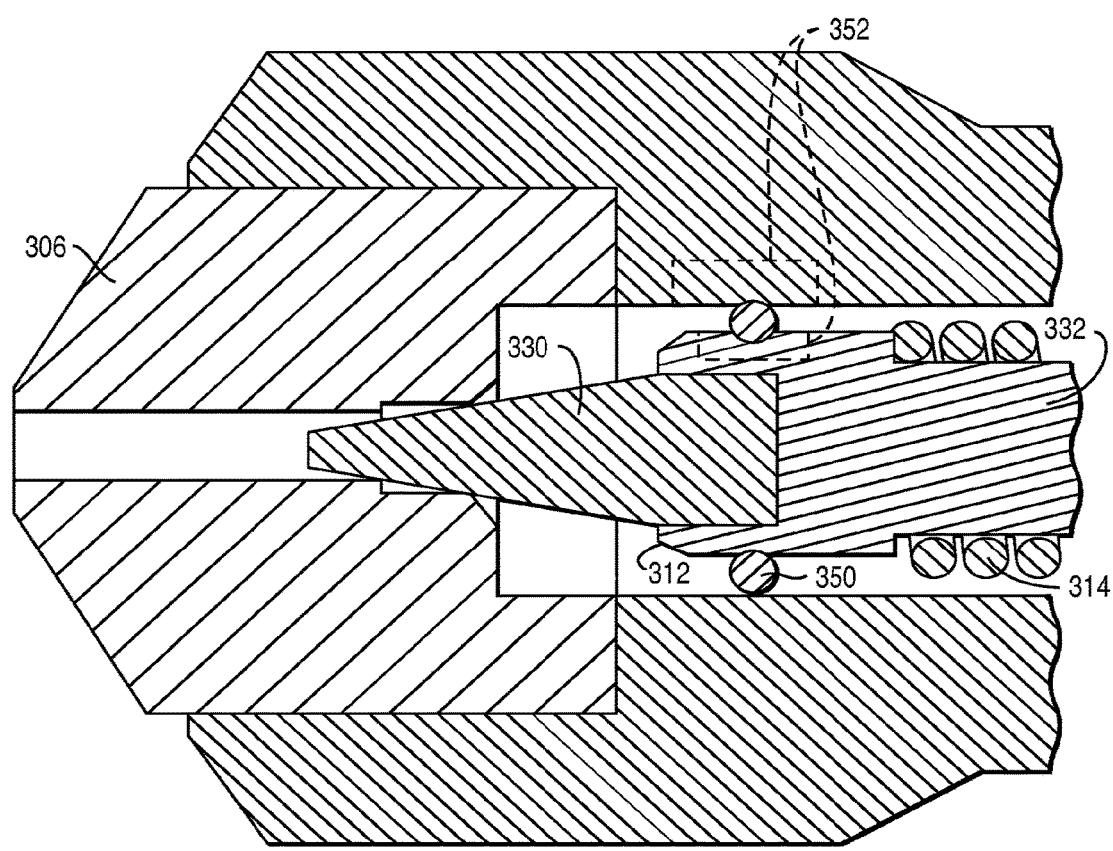
FIGS. 4A-4C illustrate implementations of the cartridge of FIG. 3 having a damping member arranged to absorb energy.

In some cases, the cartridge can be provided with a damping member to help reduce vibrations. For example, an elastomer damping member can be disposed between the head 336 and the cartridge housing 302. The damping member can absorb energy, thereby reducing vibrations that might otherwise contribute to seat 306 and poppet 312 damage. FIG. 4A illustrates an implementation in which an o-ring type gasket 350 is provided between the head 336 and the cartridge housing 302. The o-ring 350 can be supported in a ring shaped groove in the cartridge housing 302. Alternatively, the o-ring 350 can be supported on the head 336 (e.g., within a ring shaped groove in the head 336) for movement with the poppet 312. By-pass grooves 352 can be provided in the cartridge housing 302 and/or on the poppet 312 to allow fluid to flow past the o-ring 350.

Figure 4B:
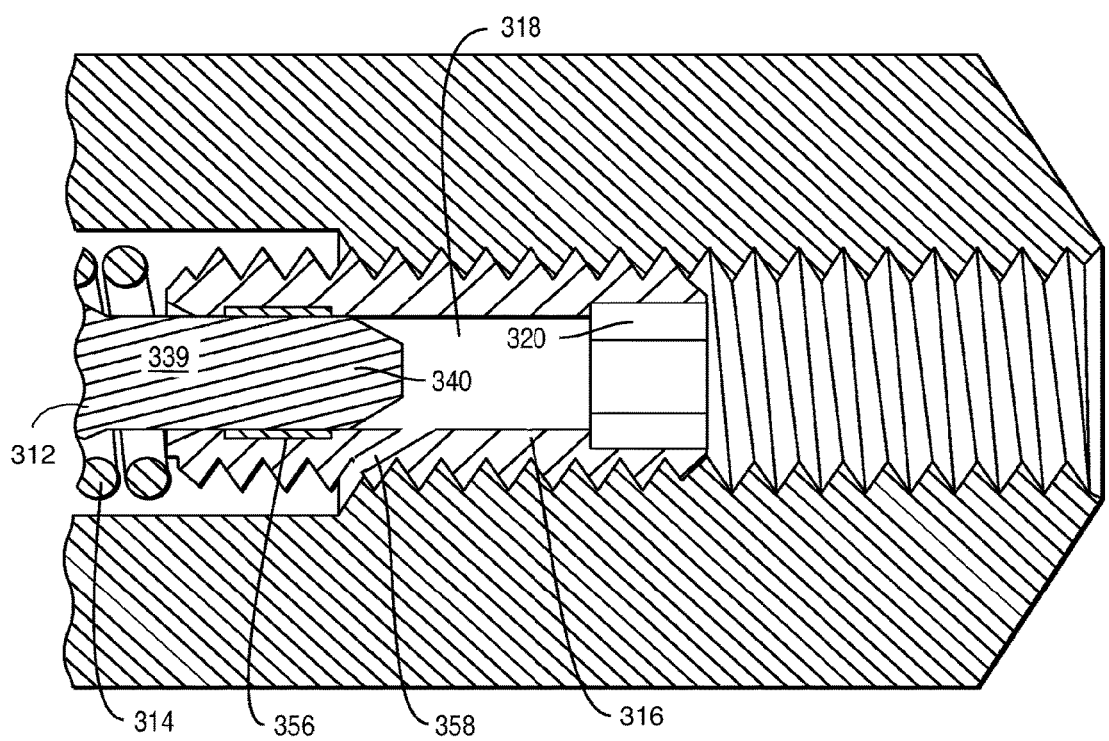
Figure 4C:
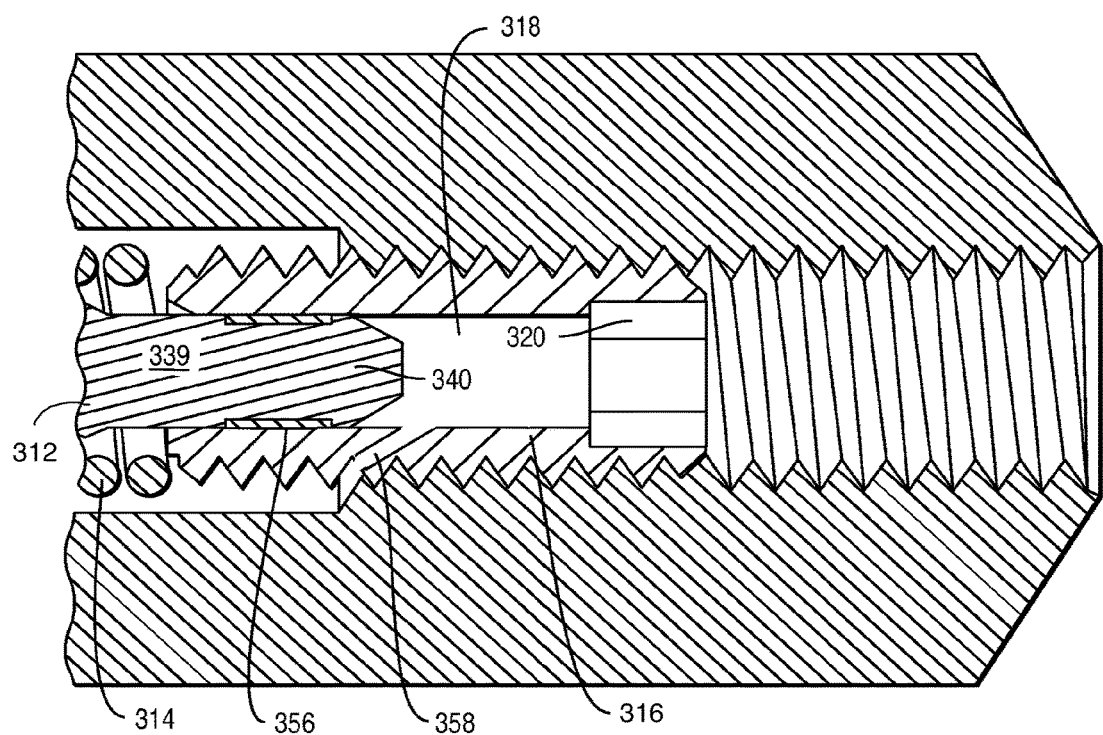

Alternatively or additionally, a damping member can be disposed between the shaft 339 and the calibration screw 316. FIGS. 4B and 4C illustrates implementations in which a damping member is positioned between the first guiding portion 340 and the calibration screw 316. The damping member can be a layer of elastomer (e.g., an elastomer sleeve 356). The elastomer sleeve 356 can be supported in a groove in the calibration screw 316, as shown in FIG. 4B. Alternatively, the elastomer sleeve 356 can be supported on the shaft 339 (e.g., within a groove in the first guiding portion 340) for movement with the poppet 312, as shown in FIG. 4C. A by-pass opening 358 can be provided in the calibration screw 316 and/or on the poppet 312 to allow fluid to flow past the elastomer sleeve 356.

Figure 5:
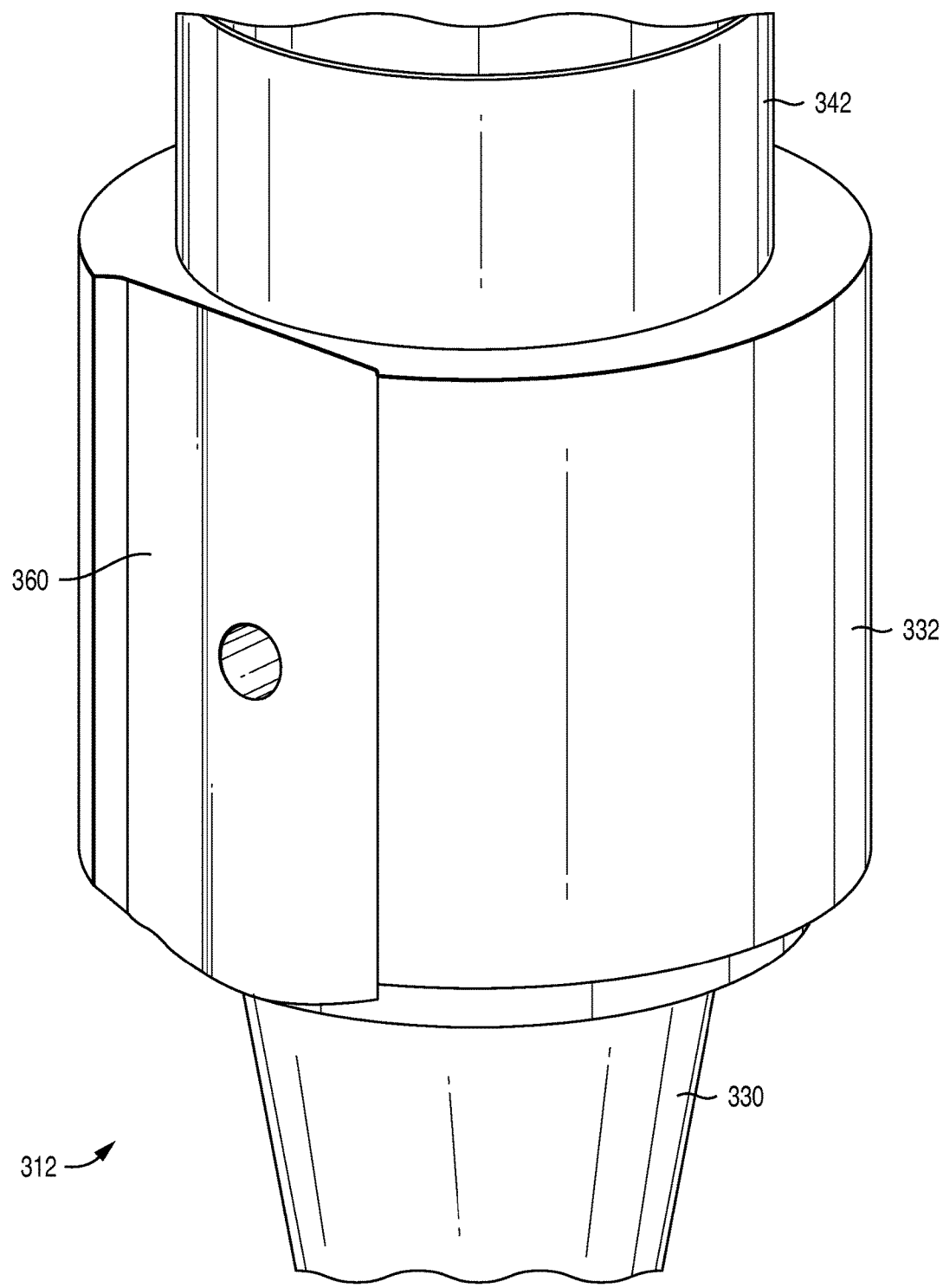
FIG. 5 is a detailed perspective view of a poppet, from the cartridge of FIG. 3, having a flow channel.
Figure 6:
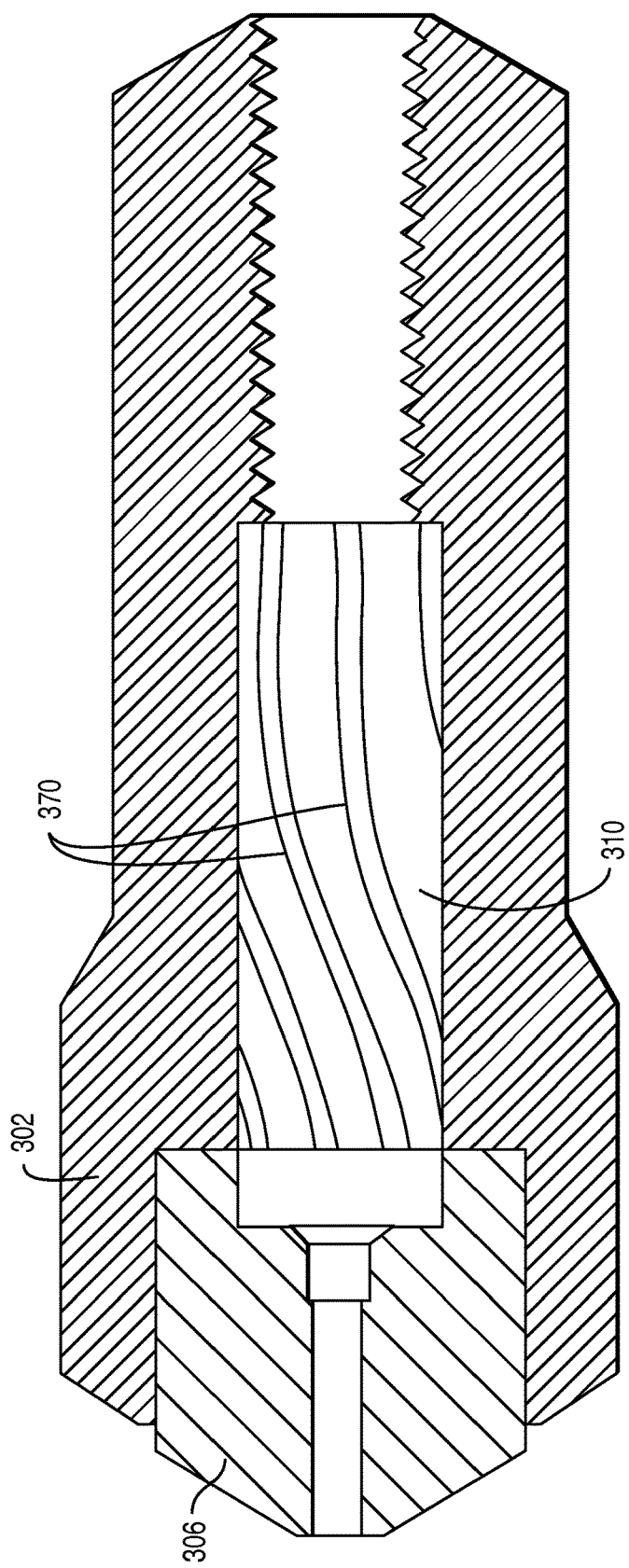
FIG. 6 is a cross-section view of a cartridge housing having helical grooves.

The high energy flow going through the static back pressure regulator 164 can cause vibration, and noise which can damage components and cause unacceptable levels of audible noise. With reference to FIG. 5, a flow channel 360 can be provided on one side of the poppet 312 to cause a slight biasing of the poppet 312 so that it does not vibrate, or so that vibration is at least reduced. Alternatively or additionally, as illustrated in FIG. 6, the inner surface of the cartridge housing 302 can be provided with helical grooves 370 to cause a vortex around the poppet 312. A vortex is a naturally stabilizing phenomenon as any side motion of the poppet 312 will result in a pressure force trying to re-center the poppet 312.

Other Implementations

Although a few implementations have been described in detail above, other modifications are possible. For example, while implementations have been described in which the poppet tip is formed of a ceramic material, the poppet tip may alternatively be formed of a metal such as stainless steel, aluminum, titanium, gold, platinum. In some cases, the poppet may comprise a gold plated metal tip. Alternatively or additionally, the tip may be formed of a polymer such as a polyimide (available as Dupont Vespel polyimide) or polyether-ether-ketone, such as PEEK™ polymer (available from Victrex PLC, Lancashire, United Kingdom).

Which an implementation has been described in which the poppet includes a tip and stem which are formed as separate parts, in some cases, the poppet tip and stem can be formed as an integral part. A single piece poppet can be formed of polymer, such as polyether-ether-ketone, or metal. In some cases, the poppet can have a single piece metal construction with gold or platinum plating.

Figure 7:
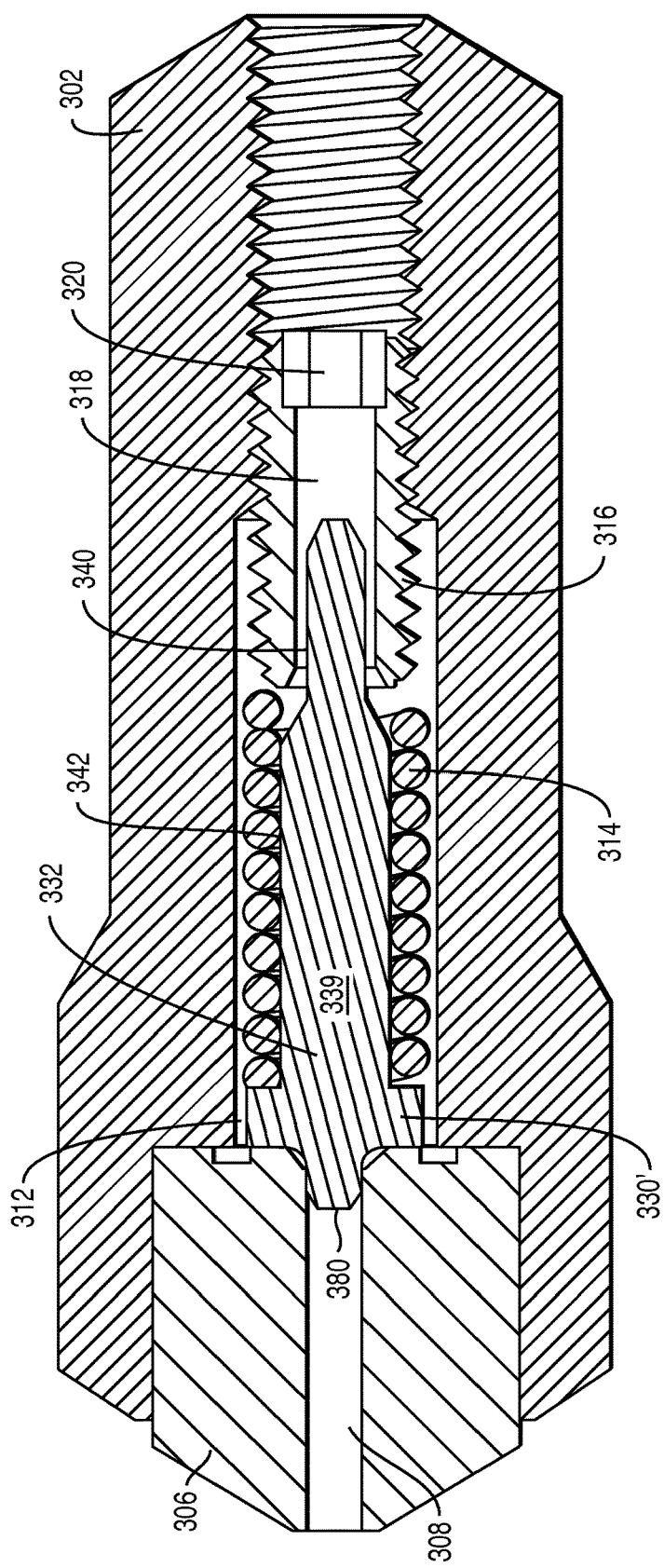
FIG. 7 is a cross-sectional view of another implementation of a static back pressure regulator cartridge having a flat tip poppet with a single piece construction.
Figure 8:
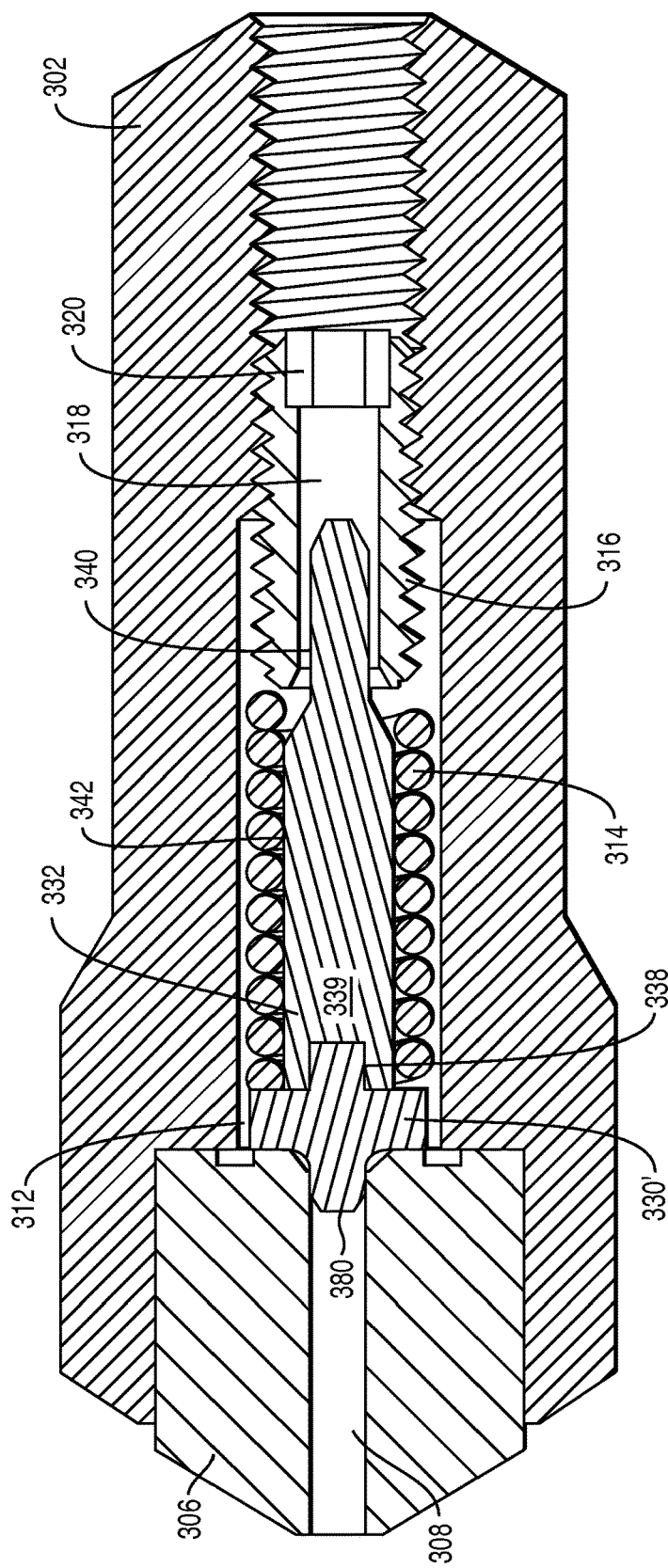
FIG. 8 is a cross-sectional view of another implementation of a static back pressure regulator cartridge having a flat tip poppet with a two-piece construction.

Although an implementation has been described which utilizes a poppet with a tapered tip, in other implementations, a poppet with a flat tip can be utilized. For example, FIG. 7 illustrates an implementation of a poppet 312 having a tip 330' with a substantially flat surface for contacting the seat 306 to inhibit fluid flow. The tip 330' also includes a boss 380 that extends into the through hole 308 in the seat 306 and helps to center the poppet 312. Because the flat tip 330 seals on a fairly large area, the load cannot concentrate to the point of yielding the seat 306. This flat tip poppet 312 also includes a stem 332 with a shaft 339 having a first guiding portion 340 to extend into the through hole 318 of the calibration screw 316 to prevent tipping. The shaft 339 also includes a second guiding portion 342 that has a diameter that is substantially the same as, or fairly close to, the inner diameter of spring 314 to inhibit buckling of the spring 314. The poppet 312 illustrated in FIG. 7 has a single piece construction, however, the flat tip poppet 312 may also have a two-piece construction in which the flat tip 330' and the stem 332 are formed as separate parts and wherein the tip 330' is received in a recess 338 formed in the stem, as illustrated in FIG. 8.

Figure 9:
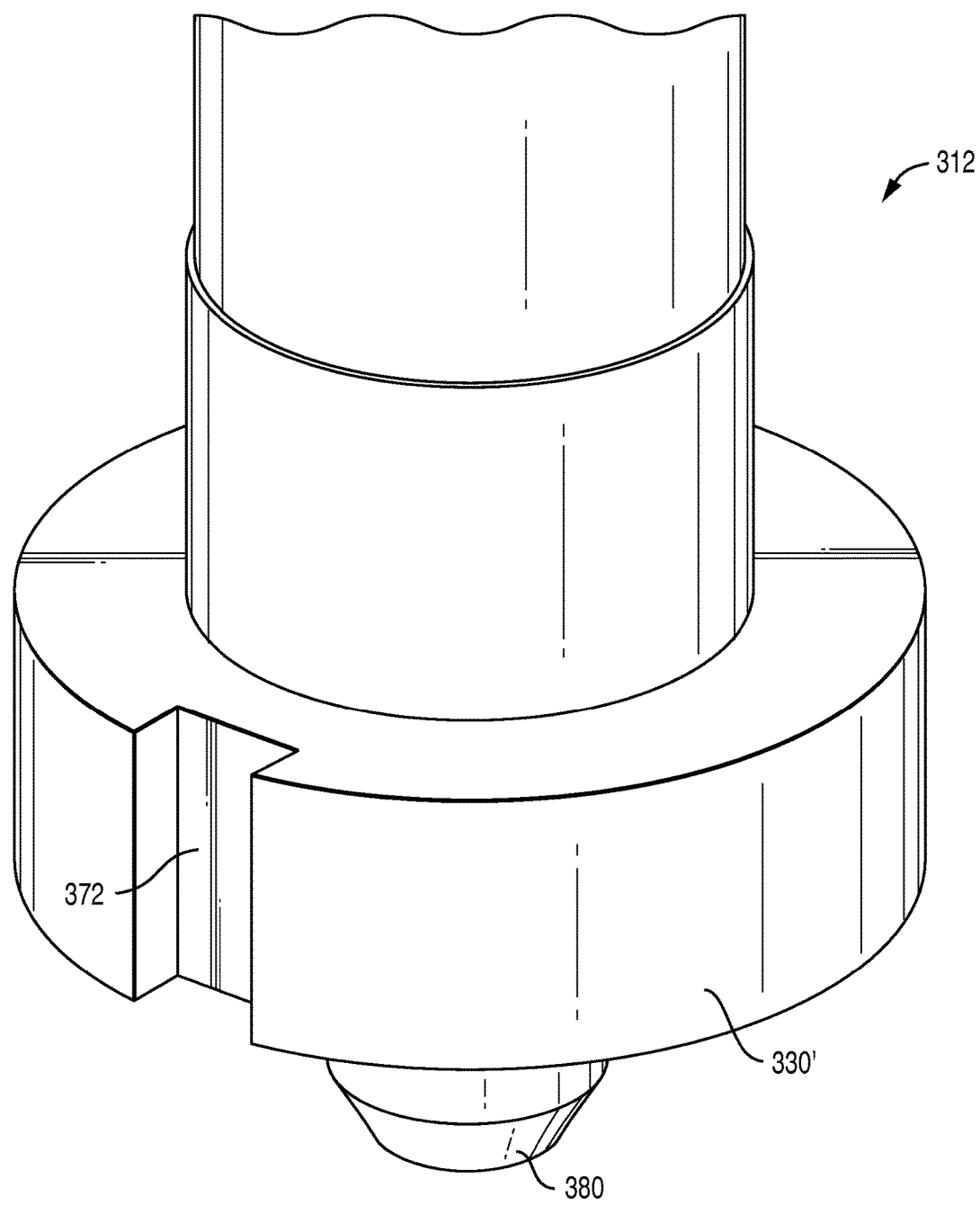
FIG. 9 is a detailed perspective view of a flat tip poppet having a flow channel.

A static pressure regulator utilizing a flat tipped poppet may also benefit from the damping and flow stabilization features discussed above. For example, FIG. 9 shows an implementation of a flat tip poppet 312 with a flow channel 372 to cause biasing of the poppet so that it does not vibrate.

Figure 10:
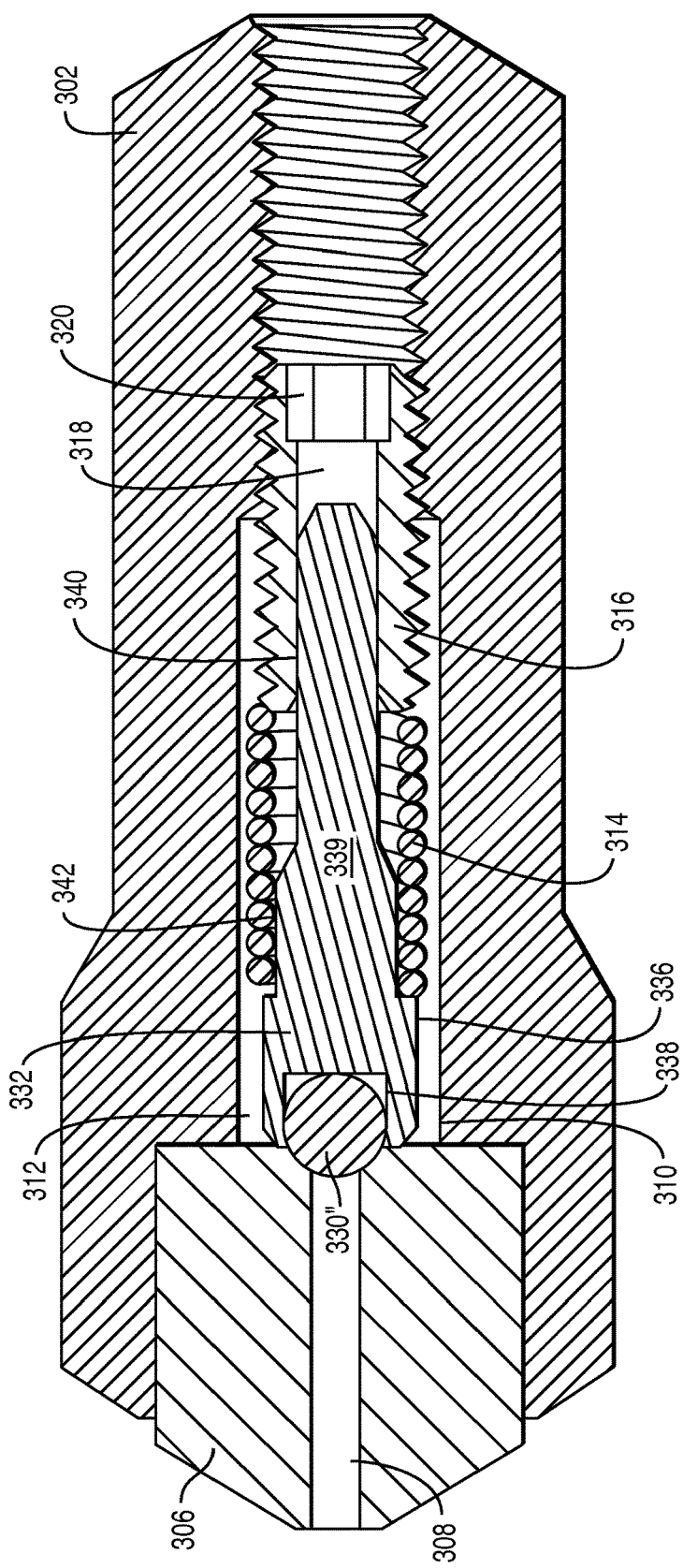
FIG. 10 is a cross-sectional view of yet another implementation of a static back pressure regulator cartridge having a poppet with a spherical tip.

Referring to FIG. 10, in yet another implementation, the poppet 312 is provided with a spherical tip 330". The spherical tip 330" resides in the recess 338 in the head 336 of the stem 332. The spherical tip 330" can be a ceramic (e.g., sapphire, ruby, zirconia) ball, or a metal ball with gold or platinum plating.

In addition, although described with respect to SFC applications, the principles can be implemented in back pressure regulators used in other applications which involve the handling of corrosive fluids and/or high velocity fluid flows. In some instances, for example, the back pressure regulators described herein may be desirable for regulating system pressure in other types of chromatography systems, such as high performance liquid chromatography (HPLC) systems.

Accordingly, other implementations are within the scope of the following claims.

What is claimed is:

1. A fluid control system comprising:
a fluid chromatography system, the fluid chromatography system comprising:
a static back pressure regulator comprising:
a main housing defining part of a fluid pathway;
a retaining nut; and
a cartridge disposed within a cavity that is defined by the main housing and the retaining nut, the cartridge including,
a seat disposed in a recess of the cartridge and defining part of the fluid pathway;
a poppet;
a spring arranged to bias the poppet toward the seat to restrict fluid flow through the fluid pathway extending through the cartridge; and
a calibration element threadingly received within an inner cartridge housing and configured to move relative to the inner cartridge housing to adjust a force applied to the poppet by the spring, wherein the calibration element includes a through hole that forms part of the fluid pathway,
wherein the poppet comprises a first guiding portion that extends into the through hole of the calibration element and inhibits tipping of the poppet relative to the seat, and
wherein the main housing is configured to receive liquid $CO_2$ from an inlet port disposed within the main housing, and
wherein the poppet includes a conical portion that contacts the seat and has an included angle greater than or equal to 20 degrees and less than or equal to 60 degrees.

2. The static back pressure regulator of claim 1, wherein the poppet further comprises a second guiding portion that extends into the spring and thereby inhibits buckling of the spring.

3. The static back pressure regulator of claim 1, further comprising a damping member arranged to absorb energy and inhibit vibration of the poppet.

4. The static back pressure regulator of claim 3, wherein the poppet is disposed within the cavity, and wherein the damping member is disposed between the calibration element and the poppet.

5. The static back pressure regulator of claim 4, wherein the damping member comprises an o-ring gasket.

6. The static back pressure regulator of claim 3, wherein the damping member is formed of an elastomer.

7. The static back pressure regulator of claim 3, wherein the damping member is disposed between the calibration element and the first guiding portion of the poppet.

8. The static back pressure regulator of claim 1, wherein the poppet has a flow channel defined by a planar flat extending along a side of the poppet so as to cause a biasing of the poppet, as fluid flows through the fluid pathway, such that vibration of the poppet is inhibited.

9. The static back pressure regulator of claim 1, wherein the poppet is disposed within the cavity, and wherein the cartridge has helical grooves along the cavity to cause a vortex around the poppet, as fluid flows through the fluid pathway, such that vibration of the poppet is inhibited.

10. The static back pressure regulator of claim 1, wherein the poppet comprises:
a tip; and
a stem comprising the first guiding portion.

11. The static back pressure regulator of claim 10, wherein the stem defines a tip recess for receiving the tip.

12. The static back pressure regulator of claim 10, wherein the stem is integral with the tip.

13. The static back pressure regulator of claim 10, wherein the tip is at least partially formed of a chemically resistant ceramic.

14. The static back pressure regulator of claim 13, wherein the chemically resistant ceramic is selected from the group consisting of zirconia, ruby, and sapphire.

15. The static back pressure regulator of claim 1, wherein the poppet comprises a metal plating.

16. The static back pressure regulator of claim 15, wherein the metal plating is selected from the group consisting of a gold plating and a platinum plating.

17. The static back pressure regulator of claim 1, wherein the seat is at least partially formed of a polymer.

18. The static back pressure regulator of claim 17, wherein the polymer is selected from the group consisting of polyimide and polyether-ether-ketone.

19. The static back pressure regulator of claim 1, further comprising a protrusion that extends from an end of the calibration element into the spring such that the protrusion is disposed between the poppet and the spring.

20. The static back pressure regulator of claim 1, wherein the first guiding portion of the poppet extends into the through hole when the poppet is in a proximal-most position relative to the calibration element and when the poppet is translated distally relative to the calibration element.

21. The static back pressure regulator of claim 1, wherein the spring exerts sufficient force to allow the static back pressure regulator to regulate pressures of at least 1100 psi.

22. A fluid control system comprising:
a fluid chromatography system, the fluid chromatography system comprising:
 a static back pressure regulator comprising:
  a main housing defining part of a fluid pathway;
  a retaining nut; and
  a cartridge disposed within a cavity that is defined by the main housing and the retaining nut, the cartridge including,
   a seat disposed in a recess of the cartridge and defining part of the fluid pathway;
   a poppet;
   a spring arranged to bias the poppet toward the seat to restrict fluid flow through the fluid pathway extending through the cartridge; and
   a calibration element threadingly received within an inner cartridge housing and configured to move relative to the inner cartridge housing to adjust a force applied to the poppet by the spring,
  wherein the calibration element includes a through hole that forms part of the fluid pathway,
  wherein the poppet comprises a first guiding portion that extends into the through hole of the calibration element and inhibits tipping of the poppet relative to the seat, and
  wherein the main housing is configured to receive liquid CO2 from an inlet port disposed within the main housing,
  wherein the poppet further comprises a tip, and wherein the tip is at least partially formed of a material selected from the group consisting of zirconia, ruby, and sapphire.

23. A fluid control system comprising:
a fluid chromatography system, the fluid chromatography system comprising:
 a static back pressure regulator comprising:
  a main housing defining part of a fluid pathway;
  a retaining nut; and
  a cartridge disposed within a cavity that is defined by the main housing and the retaining nut, the cartridge including,
   a seat disposed in a recess of the cartridge and defining part of the fluid pathway;
   a poppet;
   a spring arranged to bias the poppet toward the seat to restrict fluid flow through the fluid pathway extending through the cartridge; and
   a calibration element threadingly received within an inner cartridge housing and configured to move relative to the inner cartridge housing to adjust a force applied to the poppet by the spring, wherein the calibration element includes a through hole that forms part of the fluid pathway,
  wherein the poppet comprises a first guiding portion that extends into the through hole of the calibration element and inhibits tipping of the poppet relative to the seat, and
  wherein the main housing is configured to receive liquid CO2 from an inlet port disposed within the main housing,
  wherein the poppet further comprises a metal plating, and wherein the metal plating is selected from the group consisting of a gold plating and a platinum plating.

24. A fluid control system comprising:
a fluid chromatography system, the fluid chromatography system including a plurality of supercritical fluid chromatography manager modules, at least one of the plurality of supercritical fluid chromatography manager modules including a static back pressure regulator, the static back pressure regulator comprising:
 a main housing defining part of a fluid pathway;
 a retaining nut; and
 a cartridge disposed within a cavity that is defined by the main housing and the retaining nut, the cartridge including,
  a seat disposed in a recess of the cartridge and defining part of the fluid pathway;
  a poppet;
  a spring arranged to bias the poppet toward the seat to restrict fluid flow through the fluid pathway extending through the cartridge; and
  a calibration element threadingly received within an inner cartridge housing and configured to move relative to the inner cartridge housing to adjust a force applied to the poppet by the spring, wherein the calibration element includes a through hole that forms part of the fluid pathway,
 wherein the poppet comprises a first guiding portion that extends into the through hole of the calibration element and inhibits tipping of the poppet relative to the seat, and
 wherein the main housing is configured to receive liquid CO2 from an inlet port disposed within the main housing.

25. A static back pressure regulator comprising:
a main housing defining part of a fluid pathway;
a retaining nut; and
a cartridge disposed within a cavity that is defined by the main housing and the retaining nut, the cartridge including,
 a seat disposed in a recess of the cartridge and defining part of the fluid pathway;
 a poppet;
 a spring arranged to bias the poppet toward the seat to restrict fluid flow through the fluid pathway extending through the cartridge; and
 a calibration element threadingly received within an inner cartridge housing and configured to move relative to the inner cartridge housing to adjust a force applied to the poppet by the spring, wherein the calibration element includes a through hole that forms part of the fluid pathway,
wherein the poppet comprises a first guiding portion that extends into the through hole of the calibration element and inhibits tipping of the poppet relative to the seat, and
wherein the main housing is configured to receive liquid CO2 from an inlet port disposed within the main housing,
wherein the poppet has a flow channel defined by a planar flat extending along a side of the poppet so as to cause a biasing of the poppet, as fluid flows through the fluid pathway, such that vibration of the poppet is inhibited.

* * * * *